(12) United States Patent
Schneider et al.

(10) Patent No.: US 6,413,950 B1
(45) Date of Patent: Jul. 2, 2002

(54) PHARMACEUTICAL PREPARATION CONTAINING DITHRANOL

(75) Inventors: Jürgen Schneider, Angersdorf; Wolfgang Wohlrab, Halle; Reinhard Neubert, Halle; Christoph Huschka, Halle; Dieter Koegst; Gerhard Fries, both of Osterweddingen, all of (DE)

(73) Assignee: esparma GmbH (DE)

( * ) Notice: Subject to any disclaimer, the term of this patent is extended or adjusted under 35 U.S.C. 154(b) by 0 days.

(21) Appl. No.: 09/913,863

(22) PCT Filed: Feb. 22, 2000

(86) PCT No.: PCT/EP00/01421

§ 371 (c)(1),
(2), (4) Date: Sep. 17, 2001

(87) PCT Pub. No.: WO00/50018

PCT Pub. Date: Aug. 31, 2000

(30) Foreign Application Priority Data

Feb. 26, 1999  (DE) .......................................... 199 08 487

(51) Int. Cl.⁷ ............................................... A61K 31/66
(52) U.S. Cl. ....................................................... 514/145
(58) Field of Search .................................. 514/75, 145

(56) References Cited

U.S. PATENT DOCUMENTS 3,881,000 A   4/1975   Freidmann et al.
5,358,716 A   10/1994  Laugier et al.

FOREIGN PATENT DOCUMENTS

DE    2 302 125       7/1974
DE    42 31 636 A1    3/1994

OTHER PUBLICATIONS

International Search Report for PCT/EP00/01421 dated Oct. 11, 2000.

*Primary Examiner*—William R. A. Jarvis
*Assistant Examiner*—Vicki Kim
(74) *Attorney, Agent, or Firm*—Leydig, Voit & Mayer, Ltd.

(57) ABSTRACT

The invention relates to a pharmaceutical preparation in a make-up which is suited for external application and which contains a dithranol derivative as an active ingredient.

6 Claims, No Drawings

PHARMACEUTICAL PREPARATION CONTAINING DITHRANOL

This application is a 371 of PCT/EP00/01421 filed Feb. 22, 2000.

The invention concerns a pharmaceutical preparation in a presentation form suitable for topical application, which contains phosphoric acid esters of dithranol and its use for low irritation treatment of psoriasis.

Dithranol is one of the most proven drugs for treatment of psoriasis in dermatology. Psoriasis is still categorized among dermatoses with uncertain ethology. For this reason various preparations are employed for classical external treatment, among them ones containing dithranol, salicylic acid or urea. An important disadvantage of current pharmaceutical preparations that contain dithranol is the use of lipophilic bases due to the high lipophilicity of the active agent, from which it can penetrate into the diseased, less lipophilic regions of the skin only with great difficulty. Usually, lipophilic ointment bases are used as vehicles for dithranol. The active agent is not soluble in water and can only be partially incorporated into aqueous formulations, if larger amounts of surfactants are added, and the stability of the active agent is low here. The good therapeutic efficacy of dithranol is, however, offset by its strong staining property, which leads to low acceptance among patients and to considerable purification problems particularly with clinical treatment. Studies of the mode of action of dithranol have been concentrated on explaining the processes of radical formation in vivo. These processes are very complex in nature, but suggest that in particular the oxidation of anthrone to anthraquinone progresses via radical intermediates and thus can also be considered as proof of the efficacy of phototherapeutic treatment methods.

Based on this, i.e., on the fact that dithranol is still a very effective drug for treatment of psoriasis (for example, W. C. Marsch, DAZ, 1995, 135(38), 3498–3499) there have been numerous attempts to derivatize it (K. K. Mustakallio, Acta Derm. Venerol. (Stockh.), 1992, 172 Suppl., 7–9). The greater portion of all of the studies in this case has been concentrated on derivatives that have new substituents chiefly in position 10. It was shown that the antipsoriatic efficacy of compounds is linked to easy homolytic cleavability of the methylene proton bond in position 10 of the anthrone parent compound. In this way it becomes understandable that of the large number of new derivatives with substituents in position 10 only the monosubstituted anthrone derivatives have biological efficacy that is in some cases higher than that of dithranol itself An important disadvantage of all of the position 10 substituted derivatives is: they do not have any significant improvement of the penetration properties into the psoriatically diseased hydrophilic regions of the skin than the pure active agent dithranol.

Based on this, a task of this invention was to propose a new pharmaceutical preparation in a presentation form suitable for topical application, which contains dithranol in a form that allows clearly improved penetration into psoriatically diseased hydrophilic regions of the skin than was possible up to now.

This object preferably is achieved by the characterizing features of the present invention. Advantageous embodiments and further developments of the invention will be apparent from the description provided herein.

Thus, in accordance with the invention, a pharmaceutical preparation that contains phosphoric acid esters of dithranol as active agent is proposed. The phosphoric acid esters of dithranol that are contained in the pharmaceutical preparation in accordance with the invention are defined by the following general formulas I through IV,

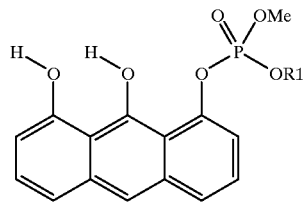

Formula I: 1-Phosphoryl-8-hydroxy-9-anthrol

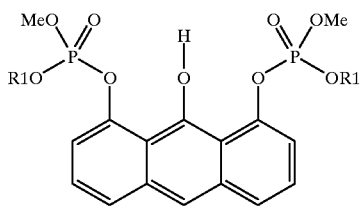

Formula II: 1,8-Diphosphoryl-8-hydroxy-9-anthrol

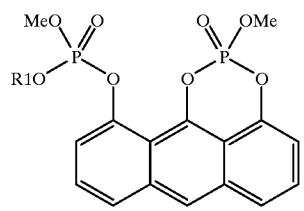

Formula III: 1-Phosphorylanthrol-8,9-cyclophosphate

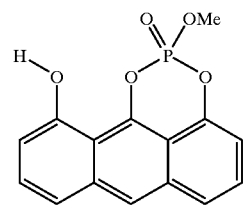

Formula IV: 8-Hydroxyanthrol-1,9-cyclophosphate
in which $R^1$ is selected from among H, aryl groups, for example phenyl and substituted homologs, alkyl groups, for example methyl, ethyl, including higher homologs like dodecyl, and Me, especially an alkali metal or alkaline earth metal. Here it is preferred if the residue $R^1$ is hydrogen and potassium is present as alkali metal. In numerous studies it proved to be particularly advantageous when the active agent is defined by general formula IV where again the metal is potassium and $R^1$ is hydrogen.

It should be particularly emphasized in regard to the pharmaceutical preparations in accordance with the invention that the physicochemical properties of the active agents that they contain can be varied via the type of cationic components and the number of phosphate residues on the dithranol. In the form of simple metal salts with monovalent or polyvalent metal cations they are readily to moderately water soluble. In this way a targeted change is possible via the type of counterion of the phosphate residue without the phosphate structure as such having to be varied. Here the hydrophilicity of these compounds is proportional to the number of phosphate residues and thus the number of counterions. Changing the hydrophilic/lipophilic behavior is also directly possible via the phosphate structure. The highest hydration is achieved as the monoester or diphosphoric acid ester on an anthrol residue. However, cyclic anthrol phosphate structures (general formulas III and IV), which are esterified cyclically in position 9 and optionally in position 8 with another phosphoryl residue, are also possible. It should be particularly emphasized that through the great variety of structures and combinations of these phosphoric acid esters it becomes possible to make available prodrug forms in which the active agent is homogeneously distributed both in aqueous as well as in water-free preparations is present in a micellarly dissolved form or in suspended form. Preferably, the pharmaceutical preparation contains 0.1–20 wt % of the active agent, especially preferably 0.5–5 wt % of the active agent. The preparation of such a pharmaceutical preparation in which the active agent is present in homogeneously distributed or micellarly dissolved form or is suspended in an aqueous or water-free formulation is basically known from the prior art. In this regard reference is made to H. D. Dörfler, "Surface and colloid chemistry" [in German], VCH Verlags-gesellschaft, Weinheim, 1994.

With the new pharmaceutical preparation, which contains prodrugs based on phosphoric acid esters, one basically has new application forms for treatment of psoriasis. With the prodrugs in accordance with the invention the active agent can penetrate in a targeted fashion into the psoriatically diseased regions of the skin from galenically acceptable formulations, where it becomes completely released in the region of the epidermis/dermis. However, since no detectable penetration of the prodrugs from aqueous formulations into undiseased regions of the skin is detected and thus their irritation can be prevented, these drugs are excellently suitable for treatment of psoriasis. Thus, with the prodrugs in accordance with the invention a new route in the treatment of psoriasis becomes possible, by making available one of the most effective active agents in treatment by means of wash solutions, lotions or gel-like formulations. Here it is decisive that these applications very largely take place without mechanical stress on the injured and thus irritation-intolerant skin. It is possible through bathing, swabbing or other moisturization routines or general application of gels to generate an appropriate difference of concentration of prodrug from the aqueous phase to the cutis, so that penetration of active agent into the skin is triggered in the desired way. Thus it can be controlled via the choice of prodrug corresponding to the purpose, its concentration in the formula itself and also via the time of contact with these preparations. Appropriate additives like urea promote rapid keratinolysis, favor the hydration of the stratum corneum in cases of severe scaling or lesions or favor the structurization within the epidermis for an improvement of penetration into the corium. These factors can be adjusted individually according to the type and severity of psoriatic damage with each individual patient and thus an optimal matching of the treatment regime can take place.

Possibilities for whole body therapy, including bath additives, or for topical therapy include wash solutions, sols for spraying on diseased skin regions or base solutions for immersion of skin bandages, as well as gels. A combination with UV A-UV B phototherapy, as before, suggests itself as a treatment routine, as a supplement to other systemic therapies, with the goal of rapid and effective treatment of lesions. The structurally determined variability of the solubility of the phosphoric acid esters of dithranol is of decisive advantage for their use as a prodrug. With this there come many new possibilities for better adjusting the formulations to the requirements of different clinical conditions in patients.

The invention is illustrated below by means of several preparation examples for the active agents and examples of formulations.

EMBODIMENT EXAMPLE 1

Preparation of 1-Phosphoryl-8,9-dihydroxyanthrol (Potassium Salt)

At room temperature and under an argon atmosphere 0.1 mol potassium methylate is stirred into a mixture of 0.1 mol dithranol in 300 mL water-free toluene. The solution turns from yellow to wine red. By applying a weak vacuum the methanol formed during the formation of the potassium dithranolate is removed by distillation, while stirring. Then the toluene is distilled out until the product is dry.

The reaction residue is mixed with about 300 mL dioxane and cooled down to 10° C. in an ice bath while stirring 0.1 mol phosphoryl chloride in 100 mL of the same solvent is slowly added so that the internal temperature does not rise above 15° C. The mixture is stirred for another hour, the external cooling is removed and stirring is continued for another 2 h at room temperature. Then the potassium chloride is filtered under inert conditions out via a tube frit and rinsed with a little dioxane. The filtrate is slowly hydrolyzed with 0.4 mol $K_2CO_3$ in about 500 mL distilled water, with external ice cooling. The internal temperature in this case must not rise above 25° C. The residue is evaporated under a vacuum until dry, the crude product is taken up with dry dioxane and recrystallized under an argon atmosphere. The potassium salts of 1-phosphoryl-8-hydroxyanthrol (main product, see formula IV) and 8-hydroxyanthrol-1,9-cyclophosphate are separated by fractional crystallization. The products are then dried in a vacuum over $P_4O_{10}$. The salts have a slight yellow gray color. They melt, with decomposition, above 200° C.

| | | | | |
|---|---|---|---|---|
| $^{31}P$ NMR spectrum in dioxane/water: | −3.5 ppm (singlet) | | | |
| Capillary electrophoresis at pH 8: | 1 product signal of high effective conductivity | | | |
| UV/VIS (in water): | typical anthracene spectrum sharp absorption at about 257 nm and absorption with benzoid alpha band structure with maximum at about 372 nm | | | |
| Element analyses*: | $C_{14}H_{10}O_6PK$ | | (M = 344.31 g/mol) | |
| | C: | H: | O: | P: |
| Calculated (%): | 48.84 | 2.93 | 27.88 | 9.00 |
| Found (%): | 49.17 | 3.08 | 28.04 | 8.85 |

*(very poorly combustible)

EMBODIMENT EXAMPLE 2

Preparation of 1-Dodecylphosphoryl-8-hydroxy-9-anthrone (Potassium Salt)

0.05 mol dithranol is present in about 300 mL dry dioxane in a 500 mL three neck flask. 0.05 mol potassium methylate is added under inert conditions with stirring, and the color of the reaction solution changes from yellow orange to violet and then to dark brown. By application of a slight vacuum of 150 torr and mild heating to about 50° C., the resulting methanol is removed from the reaction mixture over 2 h. Then dodecyl dichlorophosphate (0.05 mol) in 50 mL dry dioxane is added to this solution under inert conditions. The reaction is brought to completion over 3 h with stirring and slow heating of the reaction mixture to 60° C., and the color of the reaction solution changes from dark brown to dark yellow. The potassium chloride, which precipitates in voluminous amount, is filtered out via a tube frit under inert conditions and washed with a little dry dioxane. The dioxane of the combined filtrates is distilled until dry on a rotary evaporator and then taken up with a little pentane in order to remove traces of potassium chloride. After filtration and distillation of the pentane there remains a brown viscous product, which is hydrolyzed with 0.1 mol potassium hydrogen carbonate dissolved in a solvent mixture of 100 mL each distilled water and methanol. The resulting potassium salt of 1-dodecylphosphoryl-8-hydroxy-9-anthrol is purified by preparative HPLC on RP-8 phase in a solvent mixture of acetonitrile and distilled water. The product phase is processed by distillation and gently dried. There remains a yellowish green viscous oil that does not tend to crystallize. The signals of the $^1$H NMR spectrum (acetone-d6) correspond to the expected values for the dodecyl residue and the anthracene ring system.

| $^{31}$P NMR spectrum (methanol-d4): | −7.45 ppm (singlet) | | |
|---|---|---|---|
| UV/VIS (in methanol): | typical anthracene spectrum sharp absorption at 260 nm and absorption with benzoid alpha band structure at 400 nm | | |
| Element analyses*: | $C_{26}H_{34}O_6PK$ | (M = 512.62 g/mol) | |
| | C: | H: | P: |
| Calculated (%): | 60.91 | 6.69 | 6.04 |
| Found (%): | 61.06 | 6.58 | 5.58 |

*(very poorly combustible)

EMBODIMENT EXAMPLE 3

Preparation of 1-Diphenylphosphoryl-8-hydroxy-9-anthrone 0.05 mol dithranol is present in about 300 mL dry dioxane in a 500 mL three neck flask. 0.5 mol potassium methylate is added under inert conditions with stirring, and the color of the reaction solution changes from yellow orange to violet and then to dark brown. By application of a slight vacuum of 150 torr and mild heating to about 50° C. the resulting methanol is removed from the reaction mixture over 2 h. Then diphenyl chlorophosphate (0.05 mol) in 50 mL dry dioxane is added to this solution under inert conditions. The reaction is brought to completion over 12 h with stirring and slow heating of the reaction batch to 100° C., and the color of the reaction solution changes from brown to green-yellow. The highly colloidally dispersed potassium chloride that forms coagulates over two days in a form that can be filtered via tube frits. The potassium chloride is washed with a little dioxane. The purified filtrates are distilled until dry, mixed again with pentane for separation of traces of potassium chloride, filtered and again distilled until dry. The remaining reddish to orange product has a very viscous oily consistency.

This product is purified by preparative HPLC on an RP-8 phase with acetonitrile and ethanol (as gradient). The product after distilling out the solvent mixture remains as an orange to reddish viscous oil.

The $^1$H and $^{13}$C NMR spectra (acetone-d6) are overlapped in the region of the phenyl ester groups by the signals of the anthracene ring atoms of the anthrone backbone and for this reason cannot be unambiguously quantitatively evaluated. The $^{31}$P NMR spectrum is unambiguous.

| $^{31}$P NMR spectrum (methanol-d4): | −17.8 ppm (singlet) | | |
|---|---|---|---|
| UV/VIS (in methanol): | anthracene spectrum with overlapped benzene bands (absorption at 250–270 nm) | | |

Absorption with benzoid alpha band structure at 400 nm

| Element analyses*: | $C_{26}H_{19}O_6PK$ | (M$^+$ = 458.4 g/mol) | |
|---|---|---|---|
| | C: | H: | P: |
| Calculated (%): | 68.12 | 4.18 | 6.67 |
| Found (%): | 67.97 | 4.25 | 6.63 |

*(very poorly combustible)

EMBODIMENT EXAMPLE 4

Preparation of an Amphiphilic Cream with a Hydrophilic Phosphoric Acid Ester of Dithranol Preparation Glycerol monostearate 60, cetyl alcohol, medium chain length triglycerides and white mineral oil are heated in a water bath to about 60° C. and mixed portion wise with a mixture of macrogol glycerol monostearate, propylene glycol, water and the potassium salt of 1-phosphoryl-8,9-dihydroxyanthrol heated to the same temperature. The cream is continuously stirred until it cools. The water that evaporates is replaced.

This cream can then be passed through a triple roll mill at the narrowest gap. It is colorless, nearly odorless, soft and can be washed from the skin with water.

| Composition 100 g preparation contains: | |
|---|---|
| Glycerol monostearate 60 | 4.0 g |
| Cetyl alcohol | 6.0 g |
| Medium chain length triglycerides | 7.5 g |
| White petroleum jelly | 25.5 g |
| Macrogol glycerol monostearate | 7.0 g |
| Propylene glycol | 9.5 g |
| Water | 38.5 g |
| 1-Phosphoryl-8,9-dihydroxyanthrol (potassium salt) | 2.0 g |

EMBODIMENT EXAMPLE 5

Preparation of an Amphiphilic Cream with Lipophilic Phosphoric Acid Ester of Dithranol Preparation Glycerol monostearate 60, cetyl alcohol, medium chain length triglycerides, white petroleum jelly and 1-diphenylphosphoryl-8-hydroxy-9-anthrone are heated in a water bath to about 60° C. and mixed portion wise with a mixture of macrogol glycerol monostearate, propylene glycol and water heated to the same temperature. The cream is continuously stirred until it is cooled. The water that evaporates out is replaced.

This cream can then be passed through the triple roll mill at the narrowest gap. It is colorless, nearly odorless, soft and can be washed from the skin with water.

| Composition 100 g preparation contains: | |
|---|---|
| Glycerol monostearate 60 | 4.0 g |
| Cetyl alcohol | 6.0 g |
| Medium chain length triglycerides | 7.0 g |
| White petroleum jelly | 24.0 g |
| 1-Diphenylphosphoryl-8-hydroxy-9-anthrone | 2.0 g |
| Macrogol glycerol monostearate | 7.0 g |
| Propylene glycol | 10.0 g |
| Water | 40.0 g |

What is claimed is:

1. A pharmaceutical preparation in a presentation form suitable for topical application containing dithranol as active agent, wherein the preparation contains an active agent of the generals I through IV

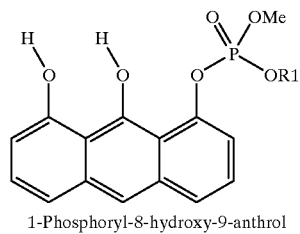

1-Phosphoryl-8-hydroxy-9-anthrol

Formula I

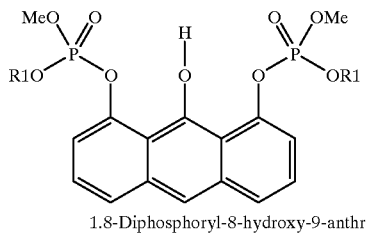

1.8-Diphosphoryl-8-hydroxy-9-anthrol

Formula II

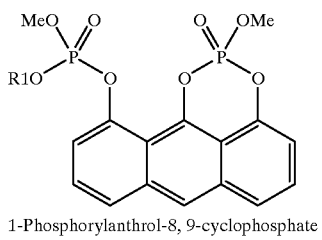

1-Phosphorylanthrol-8, 9-cyclophosphate

Formula III

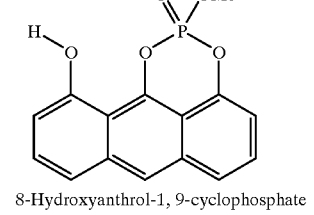

8-Hydroxyanthrol-1, 9-cyclophosphate

Formula IV in which $R^1$=H, phenyl or ethyl or dodecyl and Me is an alkali metal or alkaline earth metal.

2. A pharmaceutical preparation as in claim 1, wherein $R^1$=H and Me=K.

3. A pharmaceutical preparation as in claim 1, wherein it contains an active agent of general formula IV, where Me=K and $R^1$=H.

4. A pharmaceutical preparation as in claim 1, wherein it contains a mixture of active agents of the general formulas I through IV.

5. A pharmaceutical preparation as in claim 1, wherein 0.1–20 wt % of the active agent is present in the preparation in a form that is homogeneously distributed, micellarly dissolved or suspended in an aqueous formulation.

6. A pharmaceutical preparation as in claim 1, wherein 0.1–20 wt % of the active agent is present in the preparation in a form that is homogeneously distributed, micellarly dissolved or suspended in an essentially water-free formulation.

* * * * *